US007575742B2

(12) United States Patent
Martin et al.

(10) Patent No.: US 7,575,742 B2
(45) Date of Patent: Aug. 18, 2009

(54) METHOD OF TREATING AUTOIMMUNE DISEASES WITH INTERFERON-BETA AND IL-2R ANTAGONIST

(75) Inventors: Roland Martin, Bethesda, MD (US); Henry McFarland, Gaithersburg, MD (US); Bibiana Bielekova, Kensington, MD (US); Thomas Waldmann, Silver Spring, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 80 days.

(21) Appl. No.: 10/519,311

(22) PCT Filed: Nov. 27, 2002

(86) PCT No.: PCT/US02/38290

§ 371 (c)(1),
(2), (4) Date: Dec. 22, 2004

(87) PCT Pub. No.: WO2004/002500

PCT Pub. Date: Jan. 8, 2004

(65) Prior Publication Data

US 2005/0249704 A1 Nov. 10, 2005

Related U.S. Application Data

(60) Provisional application No. 60/393,021, filed on Jun. 28, 2002.

(51) Int. Cl.
*A61K 38/21* (2006.01)
*A61K 39/395* (2006.01)
*C07K 14/00* (2006.01)
*C07K 16/00* (2006.01)

(52) U.S. Cl. .................. 424/85.4; 424/143.1; 530/351; 530/388.22

(58) Field of Classification Search ........................ None
See application file for complete search history.

(56) References Cited

U.S. PATENT DOCUMENTS

| 5,530,101 | A | | 6/1996 | Queen et al. |
| 5,674,494 | A | | 10/1997 | Strom |
| 5,886,152 | A | * | 3/1999 | Nakatani et al. ......... 530/387.3 |
| 6,096,728 | A | | 8/2000 | Collins et al. |

FOREIGN PATENT DOCUMENTS

| GB | 2188941 | 10/1987 |
| WO | WO 89/09622 | 10/1989 |
| WO | WO 90/07861 | 7/1990 |
| WO | 93/01289 | 1/1993 |
| WO | WO 98/13067 | 4/1998 |
| WO | 00/25816 | 5/2000 |
| WO | 2004/003156 | 1/2004 |

OTHER PUBLICATIONS

Goldsby RA, et al. Kuby, Immunology. 4th Ed. 2000. W.H. Freeman and Company. New York, NY. p. 497-503.*
Jacobs LD, et al. Intramuscular interferon beta-1a for disease progression in relapsing multiple sclerosis. Annals of Neurology. 1996. vol. 39(3), p. 285-294.*
Vincenti F, et al. Interleukin-2-receptor blockade with daclizumab to prevent acute rejection in renal transplantation. New Eng. J. Med. 1998. vol. 338, p. 161-165.*
Hayosh N.S. et al. IX. Inhibition of adoptive transfer or autoimmune encephalomyelitis with a monoclonal antibody specific for interleukin 2 receptors. J. Immunol. 1987. vol. 138, p. 3771-3775.*
Bellamy et al., "The Distribution of Interleukin-2 Receptor Bearing Lymphocytes in Multiple Sclerosis: Evidence for a Key Role of Activated Lymphocytes," *Clin. Exp. Immunol.*, 61:248-256 (1985).
Giorelli et al., "IFN-beta1a Modulates the Expression of CTLA-4 and CD28 Splices in Human Mononuclear Cells: Induction of Soluble Isoforms," *J. Interferon Cytokine Res.*, 21:809-12 (2001).
"Industry News (Transplantation): FDA Approval of Zenapax for Kidney Transplants Announced," *Cancer Weekly*, p. 2 (1997).
Junghans et al., "Anti-Tac-H, a Humanized Antibody to the Interleukin 2 Receptor with New Features for Immunotherapy in Malignant and Immune Disorders," *Cancer Res.*, 50:1495-1502 (1990), abstract only.
Khoury et al., "Changes in Activated T Cells in the Blood Correlate with Disease Activity in Multiple Sclerosis," *Arch Neurol*, 57:1183-1189 (2000).
Lehky et al., "Reduction in HTLV-I Proviral Load and Spontaneous Lymphoproliferation in HTLV-I-Associated Myelopathy/Tropical Spastic Paraparesis Patients Treated with Humanized Anti-Tac," *Ann. Neurol.*, 44:942-947 (1998).
Marwick, "Scientists Recall Progress and Promise of Translational Research," *J. Natl. Cancer Inst.*, 93:13-15 (2001).
Nussenblatt et al., "Treatment of Noninfectious Intermediate and Posterior Uveitis with the Humanized Anti-Tac mAb: A Phase I/II Clinical Trial," *Proc. Natl. Acad. Sci.*, 96:7462-7466 (1999).
Paty et al., "Interferon beta-1b is effective in relapsing—remitting multiple sclerosis," *Neurology* 43:662-667, 1993.

(Continued)

*Primary Examiner*—Robert Landsman
*Assistant Examiner*—Bruce D. Hissong
(74) *Attorney, Agent, or Firm*—Klarquist Sparkman, LLP

(57) ABSTRACT

Disclosed is a method of administering an interleukin-2 receptor (IL-2R) antagonist to a subject to treat an autoimmune disease. In particular embodiments, the IL-2R antagonist is an anti-IL-2R monoclonal antibody specific for one or more chains of the IL-2R, such as the alpha-chain, for example daclizumab. In other particular embodiments the autoimmune disease is multiple sclerosis. In certain embodiments administration of interferon-beta is combined with administration of an antagonist of the IL-2R to provide significant clinical improvement in a subject with an autoimmune disease.

22 Claims, 7 Drawing Sheets

OTHER PUBLICATIONS

Posey et al., "New Drugs for 1997," www.ascp.com/public/pubs/tcp/1997/apr/newdrugs, 21pp. (1997).

"Study of Zenapax in the Treatment of Multiple Sclerosis," www.mult-sclerosis.org/news/Nov2000/ZenapaxMS, 4pp. (Nov. 2000).

Wandinger et al., "Complex Immunomodulatory Effects of Interferon-beta in Multiple Sclerosis Include the Upregulation of T Helper 1-associated Marker Genes," *Ann. Neurol.*, 50(3):349-57 (2001).

Becker et al. "Differential Gene Expression in Multiple Sclerosis Lesions Identified Using cDNA Microarrays," *Poster Abstracts / J. Neuroimmunology* 90:71 (1998) Abstract only.

Sharief et al. "Reduced expression of the inhibitor of apoptosis proteins in T cells from patients with multiple sclerosis following interferon-$\beta$ therapy," *J. Neuroimmunology* 129:224-231 (2002).

Queen et al, "A humanized antibody that binds to the interleukin 2 receptor," *Proceedings of the National Academy of Sciences of the USA*, 86(24):10029-10033 (Dec. 1989).

L'Episcopo et al., "Natural interferon-$\beta$ treatment of relapsing-remitting and secondary-progressive multiple sclerosis patients. A two-year study," *ACTA Nuerologica Scandinavica* 100:283-289 (Nov. 1999).

\* cited by examiner

METHOD OF TREATING AUTOIMMUNE DISEASES WITH INTERFERON-BETA AND IL-2R ANTAGONIST

PRIORITY CLAIM

This is the § 371 U.S. National Stage of International Application No. PCT/US2002/038290, filed Nov. 27, 2002, which was published in English under PCT Article 21(2), which in turn claims the benefit of U.S. Provisional Application No. 60/393,021, filed Jun. 28, 2002, which is incorporated by reference in its entirety.

FIELD

Pharmaceutical compounds and compositions are disclosed that are useful to treat autoimmune diseases.

BACKGROUND

An autoimmune disease is a condition that results from a pathological immune reaction against an individual's own tissues. Examples of autoimmune diseases, in which the immune system attacks otherwise healthy tissue include multiple sclerosis (MS), autoimmune uveitis, myasthenia gravis (MG), psoriasis, and rheumatoid arthritis (RA).

Multiple sclerosis (MS) is a chronic, neurological, autoimmune, demyelinating disease. MS can cause blurred vision, unilateral vision loss (optic neuritis), loss of balance, poor coordination, slurred speech, tremors, numbness, extreme fatigue, changes in intellectual function (such as memory and concentration), muscular weakness, paresthesias, and blindness. Many subjects develop chronic progressive disabilities, but long periods of clinical stability may interrupt periods of deterioration. Neurological deficits may be permanent or evanescent. In the United States there are about 250,000 to 400,000 persons with MS, and every week about 200 new cases are diagnosed. Worldwide, Miss. may affect 2.5 million individuals. Because it is not contagious, which would require U.S. physicians to report new cases, and because symptoms can be difficult to detect, the incidence of disease is only estimated and the actual number of persons with MS could be much higher.

The pathology of MS is characterized by an abnormal immune response directed against the central nervous system. In particular, T-lymphocytes are activated against the myelin sheath of the central nervous system causing demyelination. In the demyelination process, myelin is destroyed and replaced by scars of hardened "sclerotic" tissue which is known as plaque. These lesions appear in scattered locations throughout the brain, optic nerve, and spinal cord. Demyelination interferes with conduction of nerve impulses, which produces the symptoms of multiple sclerosis. Most patients recover clinically from individual bouts of demyelination, producing the classic remitting and exacerbating course of the most common form of the disease known as relapsing-remitting multiple sclerosis.

The activation and proliferation of T-lymphocytes involves the secretion of autocrine growth factors, such as interluekin-2 (IL-2) and the concomitant expression of its receptor (IL-2R) on the surface of the lymphocytes. A resting T-lymphocyte does not express IL-2R, but once activated by the appropriate antigen the cell secretes IL-2, which stimulates the cells of the immune system and up-regulates the expression of IL-2R, thus causing lymphocyte proliferation. This upregulation is believed to be involved in the immunopathogenesis of multiple sclerosis.

Several treatment options exist for treating MS. Acute bouts of neurological dysfunction are often treated with short-term administration of corticosteroids such as methylprednisilone. Interferon beta has been approved by the FDA as a treatment of MS in the United States and it is typically administered chronically in the treatment of long-term disease. The interferons are a major class of cytokine that play a role in immune activation and modulation. The putative mechanism of interferon-beta includes the inhibition of T-lymphocyte proliferation; inhibiting blood-brain-barrier permeability and T-lymphocyte transmigration into the brain by interfering with cell adhesion; and the upregulation of anti-inflammatory cytokines.

The two types of interferon-beta that are approved in the United States for use in treating MS are interferon-beta 1a and interferon-beta 1b. An interferon-beta 1b known as BETASERON® was approved as a treatment for MS in 1993 and is marketed by Berlex Laboratories, Inc. An interferon-beta 1a known as AVONEX® was approved in 1996 and is marketed by Biogen, Inc. Another interferon-beta 1a was approved in 2002 and is known as REBIF®, marketed by Serono, Inc.

According to the manufacturer's prescribing information, AVONEX® (interferon-beta) has been demonstrated to decrease the number of gadolinium (Gd)-enhanced lesions in subjects who were administered the drug for two years by up to 13% and to improve approximately 22% of subjects' Expanded Disability Status Scale (EDSS) scores. According to Samkoff, *Hosp. Phys.*, p. 21-7 (2002), REBIF® (interferon-beta) can reduce relapse rates in subjects taking the drug by 33%. According to the Physicians' Desk Reference (1996), BETASERON® (interferon-beta) has been demonstrated to reduce the exacerbation rate in subjects taking the drug by about 31%.

As can be seen, none of these drugs is highly effective in treating MS. In fact, a substantial number of individuals do not respond at all, or fail to respond over time, to interferon-beta therapy. Thus, there is an urgent need to develop more effective treatments for MS, as well as other autoimmune diseases.

IL-2R antagonists bind to the IL-2R on activated T-lymphocytes, which inhibits IL-2 from binding to the lymphocyte and thereby interferes with the IL-2 dependent proliferation of activated T-lymphocytes. One such IL-2R antagonist is known as anti-Tac, an antibody specific for the alpha chain (Tac) of the human IL-2R on activated T-lymphocytes. A particular anti-Tac antibody generically known as daclizumab is a recombinant humanized monoclonal antibody. U.S. Pat. No. 5,530,101 discloses a humanized immunoglobulin that specifically binds to a human interleukin-2 receptor. That patent is assigned to Protein Design Labs, which markets an anti-Tac pharmaceutical known as SMART®. Roche Pharmaceuticals also markets an anti-Tac pharmaceutical known as ZENAPAX® (daclizumab).

ZENAPAX® (daclizumab) is used as an immunosuppressant to inhibit allograft rejection. It is not known to be beneficial in treating MS. ZENAPAX® (daclizumab) has been shown to be effective in the treatment of human T-cell lymphotrophic virus type 1 associated myelopathy/topical spastic paraparesis (HAM/TSP). Lehky et al., *Ann. Neuro.*, 44:942-947 (1998). ZENAPAX® (daclizumab) has also been reported as an immunosuppressive agent in the treatment of posterior uveitis. Nussenblatt et al., *Proc. Natl. Acad. Sci.*, 96:7462-7466 (1999). Other anti-Tac agents include basiliximab (SIMULECT®), BT563 (see Baan et al., *Transplant. Proc.*, 33:224-2246 (2001)), and 7G8. Basiliximab has been reported to be beneficial in preventing allograft rejection, Kahan et al., *Transplantation*, 67:276-84 (1999), and treating psoriasis, Owen & Harrison, *Clin. Exp. Dermatol.*, 25:195-7 (2000). Mig beta-2 is another IL-2R antagonist, but it is specific for the beta chain of human IL-2R.

In spite of these prior therapies, the search for a more effective treatment for MS has continued. Any treatment that could delay the progression or recurrence of the disease would be enormously beneficial to people who have this disease, by reducing neurological impairment and disability. Such a treatment could also reduce health care costs, by minimizing the amount of care patients require for their MS-induced neurological disabilities.

SUMMARY

It has now been discovered that an IL-2R antagonist is effective to treat MS. In particular embodiments, the IL-2R antagonist is an anti-IL-2R monoclonal antibody, such as daclizumab.

In other embodiments, a method of treatment is disclosed in which administration of interferon-beta is combined with administration of an antagonist of the IL-2R to provide significant clinical improvement in individuals with an autoimmune disease. In particular examples, the IL-2R antagonist is an antibody, such as a monoclonal antibody, for example an anti-Tac, such as daclizumab, and the autoimmune disease is multiple sclerosis.

It has also been determined that administration of a combination of anti-Tac and interferon-beta causes the upregulation of the cytotoxic T lymphocyte-associated antigen 4 (CTLA-4), which is an inhibitory receptor of T-lymphocytes. The expression of CTLA-4 can downregulate T-cell activation, and one would expect this action to be therapeutic in an autoimmune diseases. In particular, the transmembrane CTLA-4 isoform (mCTLA-4) as opposed to the soluble isoform (sCTLA-4) is upregulated. This is surprising because interferon-beta has been reported to downregulate mCTLA-4 and upregulate sCTLA-4. Giorelli et al., *J. Interferon Cytokine Res.*, 21:809-12 (2001). This unexpected upregulation of mCTLA-4 caused by the combined administration of interferon-beta and anti-Tac may be responsible for the combined treatment's high rate of success with MS.

Accordingly, combined administration of interferon-beta and an IL-2R antagonist in a therapeutically effective combined dose is useful in treating autoimmune diseases. In particular this combination is useful in treating MS, for example initial onset of disease, relapsing-remitting, or secondary-progressive MS. The combination of these agents is also useful to treat certain symptoms of the disease, such as optic neuritis, paresthesias, or acute episodes of disease. Additionally, the combination is useful for treating subjects that have already failed to respond to interferon-beta treatment alone. In particular combinations the IL-2R antagonist is anti-Tac, for example daclizumab.

DETAILED DESCRIPTION

Figure 1:
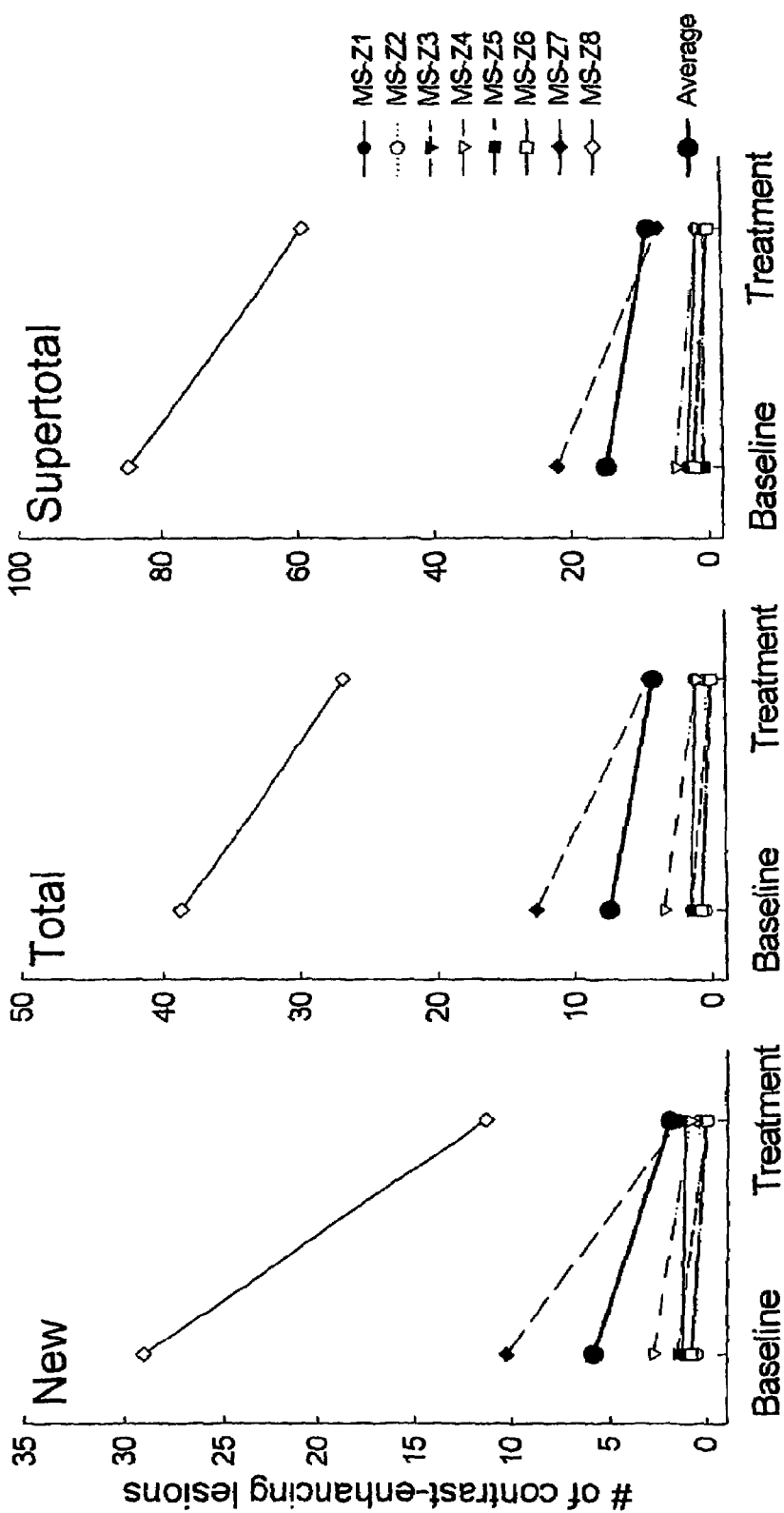
FIG. 1 is three graphs showing the changes in new, total, and supertotal contrast enhancing lesions as measured by magnetic resonance imaging (MRI) scans in subjects treated with a combination of daclizumab and interferon-beta showing the difference between a 3-month baseline period of treatment only with interferon-beta and after combination therapy in eight subjects.

Disclosed herein is a method of treating autoimmune diseases by administering a therapeutically effective dose of an IL-2R antagonist or a combination of interferon-beta and an IL-2R antagonist. In particular embodiments, the disease to be treated is multiple sclerosis. Further provided is a method in which the multiple sclerosis to be treated is a relapsing-remitting or secondary-progressive form of the disease. In particular embodiments the IL-2R antagonist is specific for the alpha chain of the human IL-2R, such as a monoclonal antibody, for example daclizumab.

Multiple sclerosis is an autoimmune disease classically described as a central nervous system white matter disorder disseminated in time and space that presents a relapsing-remitting illness in 80-85% of patients. Diagnosis can be made by brain and spinal cord magnetic resonance imaging (MRI), analysis of somatosensory evoked potentials, and analysis of cerebrospinal fluid to detect increased amounts of immunoglobulin or oligoclonal bands. MRI is a particularly sensitive diagnostic tool. MRI abnormalities indicating the presence or progression of MS include hyperintense white matter signals on T2-weighted and fluid attenuated inversion recovery images, gadolinium enhancement of active lesions, hypointensive "black holes" (representing gliosis), and brain atrophy on T1-weighted studies. Serial MRI studies can be used to indicate disease progression.

Relapsing remitting multiple sclerosis is a clinical course of MS that is characterized by clearly defined, acute attacks with full or partial recovery and no disease progression between attacks.

Secondary-progressive multiple sclerosis is a clinical course of MS that initially is relapsing-remitting, and then becomes progressive at a variable rate, possibly with an occasional relapse and minor remission.

In certain embodiments the method provided is performed with subjects who have failed to respond adequately to interferon-beta treatment alone. A failure to respond to interferon-beta treatment alone is, in some examples, demonstrated by the subject experiencing one or more exacerbations in an 18 month period of interferon-beta therapy, an increase of 1 point or more on the EDSS over 18 months of treatment, or persistence or reoccurrence of contrast enhancing lesions on brain MRI scans to at least one-half the mean of a baseline of monthly contrast enhancing lesions established over a 6-month baseline period measured prior to the beginning of the interferon-beta therapy. These examples of treatment failure are non-limiting. Other indicators of disease progression or activity known to those with skill in the art can also be used to determine whether a subject has failed to respond to interferon-beta therapy.

Interferon-beta is any beta interferon including interferon-beta 1a and interferon-beta 1b. Interferon-beta can be manufactured via means known to those skilled in the art. However, it is also approved and available for sale in the United States from several sources. Both types of interferon-beta are approved in the United States for use in treating MS. Interferon-beta 1b is available under the name BETASERON® (Berlex Labs). Interferon-beta 1a is available under the names AVONEX® (Biogen) or REBIF® (Serono).

Interferon-beta 1b is a highly purified protein that has 165 amino acids and an approximate molecular weight of 18,500 daltons. According to the manufacturer, BETASERON® (interferon-beta) is manufactured by bacterial fermentation of a strain of *Escherichia coli* that bears a genetically engineered plasmid containing the gene for human interferon-beta. The native gene was obtained from human fibroblasts and altered to substitute serine for the cystine residue found at position 17. The mechanisms by which interferon-beta 1b exerts its actions in multiple sclerosis are not clearly understood. However, it is known that the biologic response-modifying properties of interferon-beta 1b are mediated through its interactions with specific cell receptors. The binding of interferon-beta 1b to these receptors induces the expression of a number of interferon induced gene products (e.g., 2',5'-oligoadenylate synthetase, protein kinase, and indoleamine 2,3-dioxygenase) that are believed to be the mediators of the biological actions of interferon-beta 1b.

Interferon-beta 1a is a 166 amino acid glycoprotein with a predicted molecular weight of approximately 22,500 daltons. According to the manufacturer, the interferon-beta 1a known as AVONEX® is produced by recombinant DNA technology utilizing mammalian cells (Chinese Hamster Ovary cells) into which the human interferon beta gene has been introduced. The amino acid sequence of AVONEX® (interferon-beta), is identical to that of natural human interferon-beta. Interferon inducing gene products and markers including 2',5'-oligoadenylate synthetase, $\beta_2$-microglobulin, and neopterin, have been measured in the serum and cellular fractions of blood collected from patients treated with AVONEX® (interferon-beta). The interferon-beta 1a known as REBIF® has recently been approved for treatment of relapsing-remitting MS. The primary difference between AVONEX® (interferon-beta) and REBIF® (interferon-beta) is the approved method of administration-intramuscular injection for the former and subcutaneous injection for the latter.

In specific embodiments the interferon-beta administered is interferon-beta 1a or -1b, such as AVONEX® or BETASERON®. Alternatively, the interferon-beta is REBIF®. In other embodiments the interferon-beta is a combination of interferon-betas. For example, BETASERON® and AVONEX® (interferon-beta) are administered together as a cocktail, or the agents are alternated in the administration schedule.

An IL-2R antagonist is an agent that binds to the IL-2R on activated T-lymphocytes and inhibits the activity of the receptor. IR-2R antagonists include agents that bind specifically to the alpha chain (or Tac subunit) of the human IL-2R, such as daclizumab, basiliximab, BT563, and 7G8 (collectively known as anti-Tac), or agents that bind to other subunits, such Mig beta-2, which binds to the beta chain of human IL-2R.

In specific embodiments the IL-2R antagonist is anti-Tac. In some cases, the anti-Tac is daclizumab, which is marketed by Roche Pharmaceuticals as ZENAPAX® (daclizumab) and by Protein Design Labs as SMART™. Daclizumab is an immunosuppressive, humanized IgG1 monoclonal antibody produced by recombinant DNA technology that binds specifically to the alpha subunit (p55 alpha, CD25, or Tac subunit) of the human high-affinity interleukin-2 (TL-2) receptor that is expressed on the surface of activated lymphocytes. According to the product information distributed by Roche Pharmaceuticals, ZENAPAX® (daclizumab) is a composite of human (90%) and murine (10%) antibody sequences. The human sequences were derived from the constant domains of human IgG1 and the variable framework regions of the Eu myeloma antibody. The murine sequences were derived from the complementarity-determining regions of a murine anti-Tac antibody. The molecular weight predicted from DNA sequencing is 144 kilodaltons.

In other embodiments the anti-Tac is basilimax, marketed as SIMULECT® by Novartis Pharma AG. Simulect is a chimeric (murine/human) monoclonal antibody ($IgG_{1k}$), produced by recombinant DNA technology, that functions as an immunosuppressive agent, specifically binding to and blocking the alpha chain of the IL-2R on the surface of activated T-lymphocytes. According the manufacturer's product information, it is a glycoprotein obtained from fermentation of an established mouse myeloma cell line genetically engineered to express plasmids containing the human heavy and light chain constant region genes and mouse heavy and light chain variable region genes encoding the RFT5 antibody that binds selectively to the IL-2R (alpha). Based on the amino acid sequence, the calculated molecular weight of the protein is 144 kilodaltons.

In some examples, the IL-2R antagonist is a combination of anti-IL-2R agents. For example, ZENAPAX® (daclizumab) and SIMULECT® are administered together as a cocktail, or the agents are alternated in the administration schedule.

The dose of each agent (IL-2R antagonist and interferon-beta) administered is a therapeutic dose, which is a dose that will cause the combination to be therapeutically effective, or which will cause the IL-2R antagonist to be effective if administered alone. Optimizing therapy to be effective across a broad population can be performed with a careful understanding of various factors to determine the appropriate therapeutic dose. The dose of each agent administered may be different for each subject and may change over time for one subject as treatment progresses. The dose may depend on the route of administration and the schedule of treatment. The dose of each agent also may be dependent on increases or decreases in the dose of the other agent.

If the interferon-beta is interferon 1b (BETASERON®), the dosage recommended by the manufacturer is 0.25 mg by subcutaneous injection every other day. However, higher or lower doses can be used, for example from 0.006 mg to 2 mg. If the interferon-beta is interferon-beta 1a and is AVONEX®, the manufacturer's recommended dosage for the treatment of relapsing forms of multiple sclerosis is 30 µg injected intramuscularly once a week. However, higher or lower doses could be used, for example 15 to 75 µg. If the interferon-beta 1a is REBIF® (interferon-beta), the manufacturer's recommended dosage is 44 µg three times per week by subcutaneous injection. However, higher or lower doses can be used. Additionally, the dosage may be changed during the course of therapy. For example, it is suggested that REBIF® (interferon-beta) be administered at an initial dose of 8.8 µg for the first two weeks, then 22 µg for the next two weeks, and then at 44 µg for the rest of the therapy period. In specific embodiments, AVONEX® (interferon-beta) was administered at a dose of 30 µg per week or BETASERON® (interferon-beta) was administered at a dose of 0.25 mg every other day.

If the IL-2R antagonist is daclizumab the dosage in certain examples is 1 mg/kg administered every two weeks, or even once a month. However, higher or lower dosages can be used, for example the method has been performed using 2 mg/kg in a subject who did not respond to the 1 mg/kg dose. Other higher or lower dosages also could be used, such as from about 0.5 to about 8 mg/kg. It has been suggested that that serum levels of 5 to 10 µg/mL are necessary for saturation of the Tac subunit of the IL-2 receptors to block the responses of activated T lymphocytes. One of skill in the art will be able to construct an administration regimen to keep serum levels within that range, although administration resulting in higher or lower serum levels could be used. In specific embodiments ZENAPAX® (daclizumab) (daclizumab) was administered at a dosage of 1 mg/kg. In other specific embodiments ZENAPAX® (daclizumab) was administered at a dosage of 2 mg/kg.

If the IL-2R antagonist is basilimax, known as SIMULECT®, saturation binding to IL-2R (alpha) in adults is reported by the manufacturer to be maintained as long as serum levels exceed 0.2 µg/mL. One of skill in the art should be able to construct an administration regimen to keep serum levels within that range, although administration resulting in higher or lower serum levels could be used.

Interferon-beta can be administered via a number of routes, including intravenous, subcutaneous, intramuscular, topical, and intralesional administration. Interferon-beta may even be administered oromucosally as described in U.S. Pat. No. 6,361,769. Interferon-beta 1a is approved for both intramuscluar (for example AVONEX®) and subcutaneous (for example REBIF®) injection. Interferon-beta 1b is approved only for subcutaneous injection (BETASERON®). In a particular embodiment, interferon-beta 1a (AVONEX®) is administered via intramuscular injection. In other embodiments, interferon-beta 1b (BETASERON®) is administered via subcutaneous injection.

IL-2R antagonists can also be administered via several routes, for example intravenously, subcutaneously, intramuscularly, or orally. In particular embodiments daclizumab is administered intravenously.

Administration of interferon-beta also can be performed on strict or adjustable schedules. For example, interferon-beta is administered once weekly, every-other-day, or on an adjustable schedule, for example based on concentration in a subject. One of skill in that art will realize that the particular administration schedule will depend on the subject and the dosage being used. The administration schedule can also be different for individual subjects or change during the course of the therapy depending on the subject's reaction. In a particular embodiment, interferon-beta 1a is administered every other week.

Administration of IL-2R antagonists can also be on a strict or adjustable schedule. One of skill in that art will realize that the administration schedule will affect the dosage to be administered. The dosing schedule can be different for different subjects, and can be adjusted over time for individual subjects. The dosing schedule may also be different for the different IL-2R antagonists. The dosing schedule can be once a week, every other week, or once a month. Dosing can also be more or less frequent. In one embodiment daclizumab is administered every other week for one month, and then once a month. In another embodiment daclizumab is administered every other week.

The combined administration of the IL-2R antagonist and interferon-beta includes administering interferon-beta either sequentially with the IL-2R antagonist, i.e., the treatment with one agent first and then the second agent, or administering both agents at substantially the same time, i.e., an overlap in performing the administration. With sequential administration a subject is exposed to the agents at different times so long as some amount of the first agent remains in the subject when the other agent is administered. The treatment with both agents at the same time can be in the same dose, i.e., physically mixed, or in separate doses administered at the same time. In a particular embodiment Avonex is administered weekly via intramuscular injection. The first week of therapy the subject receives an intravenous infusion of ZENAPAX® (daclizumab) at the same time as the Avonex injection, with a second ZENAPAX® (daclizumab) infusion being administered two weeks later at the same time as the AVONEX® (interferon beta) injection. Thereafter ZENAPAX® (daclizumab) is administered monthly at the same time as the weekly AVONEX® (interferon beta) injection. In another embodiment BETASERON® (interferon-beta) is administered every other day via subcutaneous injection while ZENAPAX® (daclizumab) is administered every other week for one month, and then monthly, with the ZENAPAX® (daclizumab) infusion not necessarily on the same day as the BETASERON® (interferon-beta) injection.

The combined administration also may include the administration of the interferon-beta or the IL-2R antagonist in formulations or dosage regimens including other agents. Either treatment agent can be prepared as a formulation in pharmaceutically acceptable media, for example normal saline, vegetable oils, mineral oil, PBS, etc. Therapeutic preparations may include physiologically acceptable liquids, gel or solid carriers, diluents, adjuvants and excipients. Additives may include bactericidal agents, additives that maintain isotonicity, e.g. NaCl, mannitol; and chemical stability, e.g. buffers and preservatives, or the like. For parenteral administration, the agents are formulated as a solution, suspension, emulsion, or lyophilized powder in association with a pharmaceutically acceptable parenteral vehicle. Liposomes or non-aqueous vehicles, such as fixed oils, may also be used. The formulation is sterilized by techniques known in the art. In particular embodiments, AVONEX® (interferon beta) or BETASERON® (interferon-beta) and ZENAPAX® (daclizumab) are administered in the formulations supplied by and as directed by their respective manufacturers.

The following non-limiting example demonstrates that the combined administration of an IL-2R antagonist and interferon-beta exerts therapeutic effects against the autoimmune disease multiple sclerosis.

EXAMPLE 1

A clinical trial was conducted to determine the effects of the combined administration of interferon-beta and an IL-2R antagonist in subjects having relapsing-remitting or secondary-progressive multiple sclerosis.

Inclusion Criteria

Subjects included in the trial were diagnosed with either relapsing-remitting or secondary-progressive multiple sclerosis; were between the ages of 16-65; scored between 2.5 and 6.5 on the EDSS; failed to respond to interferon-beta treatment alone as demonstrated by one or more exacerbations in the 18 months prior to enrollment, an increase of 1 point or more on the EDSS over 18 months of treatment, or persistence or reoccurrence of contrast enhancing lesions on brain MRI to at least one-half the mean of baseline monthly contrast enhancing lesions over a 6-month baseline period measured prior to the beginning of interferon-beta therapy; and must have had at least 3 gadolinium enhancing lesions in the first 3 pre-combination therapy MRI scans.

Exclusion Criteria

Subjects were excluded from the trial if: diagnosed with primary-progressive MS, pre-treatment blood tests were abnormal; diagnosed with a concurrent clinically significant major disease; contraindications to monoclonal antibody therapies were observed; determined to be positive for HIV; treated with glatiramer acetate or cyclophosphamide in the 26 weeks prior to the trial, or treated with intravenous immunoglobulin (IVIg), azathioprine (AZA), methotrexate (MTX), cyclosporin, cyclophosphamide (CTC), cladribine, or mitox in the 12 weeks prior to the trial, or treated with corticosteroids or adrenocorticotrophic hormone (ACTH) in the 8 weeks prior to the trial, or treated with any other investigational drug or procedure for MS; not practicing adequate contraception; or breastfeeding.

Course of Treatment

Eight subjects were selected for inclusion in the trial of the combination therapy. For each subject a baseline 3-month period of treatment with interferon-beta (AVONEX® (interferon-beta) or BETASERON® (interferon-beta)) was established. AVONEX® (interferon-beta) was administered as indicated in the prescribing information supplied by the manufacturer at a dose of 30 µg injected intramuscularly once a week. BETASERON® (interferon-beta) was administered as indicated in the prescribing information supplied by the manufacturer at a dose of 0.25 mg injected subcutaneously every other day. Four MRI scans were performed during the baseline period to determine a baseline number of contrast enhancing lesions, one at the beginning of the period and then at the end of each month of the baseline period with the fourth coinciding with the beginning of the combination therapy. Subjects were also evaluated on the EDSS, the Scripps Neurologic Rating Scale (NRS), and various ambulation and other motor skill tests.

Combined therapy began after the 3-month baseline was established. Interferon-beta treatment was continued and, in addition, anti-Tac (ZENAPAX® (daclizumab) was administered for 5.5 months. During the first month of the combined administration ZENAPAX® (daclizumab) was administered every other week and thereafter ZENAPAX® (daclizumab) was administered once a month. ZENAPAX® (daclizumab) was administered intravenously in the manner described in the manufacturer's prescribing information at a dose of 1 mg/kg of body weight. One subject received a dose of 2 mg/kg every other week after showing no response to the 1 mg/kg dose. MRI scans were performed during the combined treatment period to determine changes in the number of contrast enhancing lesions, one every two weeks for the first six weeks of treatment, and thereafter monthly for a total of 8 MRI scans. On the same schedule subjects were also evaluated on the EDSS, the Scripps NRS, and various ambulation and other motor skill tests.

Results

Figures 2A, 2B:
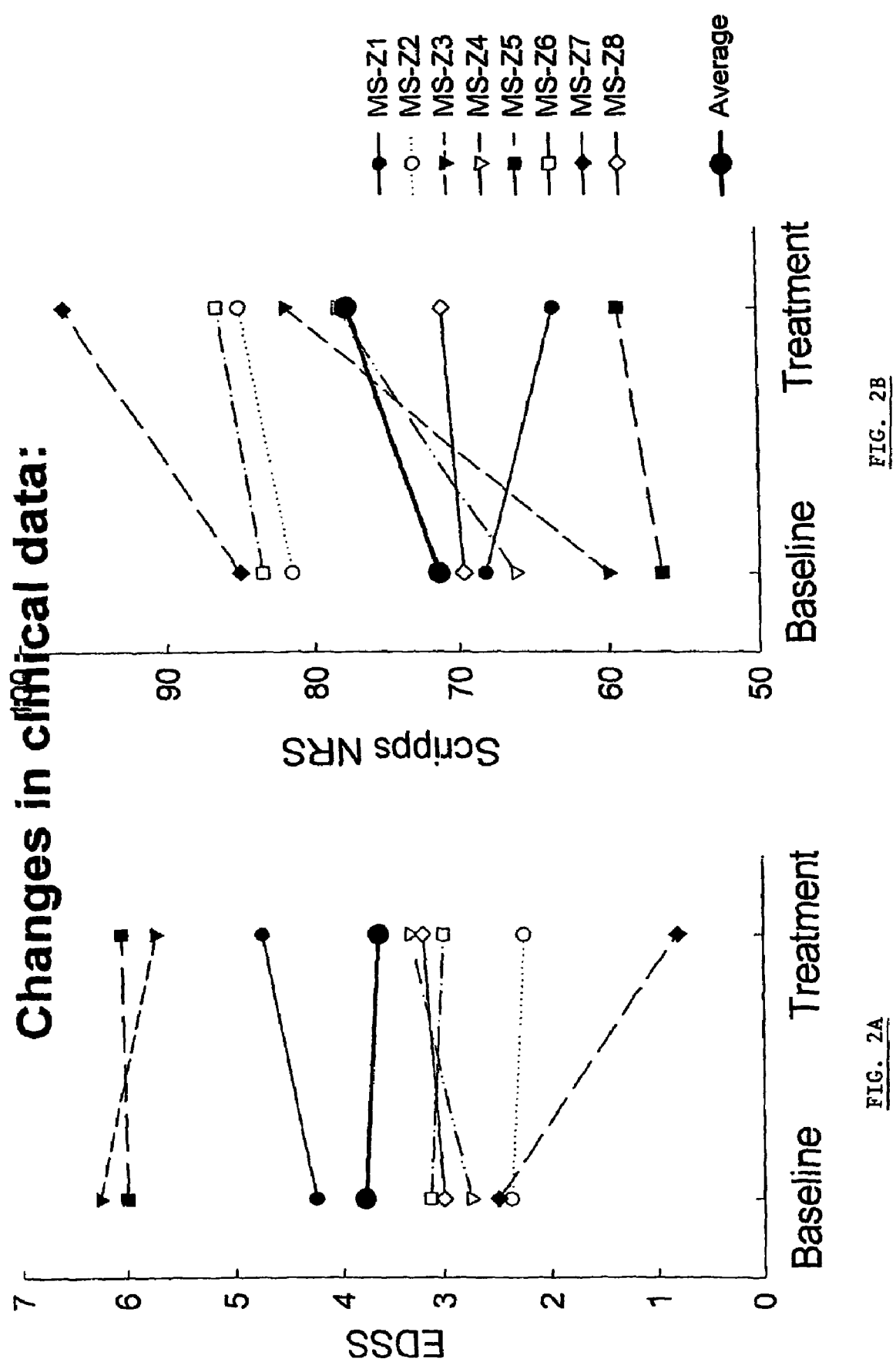
FIGS. 2A and 2B are graphs showing changes in neurological performance as measured by performance on the Expanded Disability Status Scale (EDSS) (2A) and the Scripps Neurologic Rating Scale (NRS) (2B) between the baseline period and after combination therapy for the same subjects as in FIG. 1.
Figures 3A, 3B:
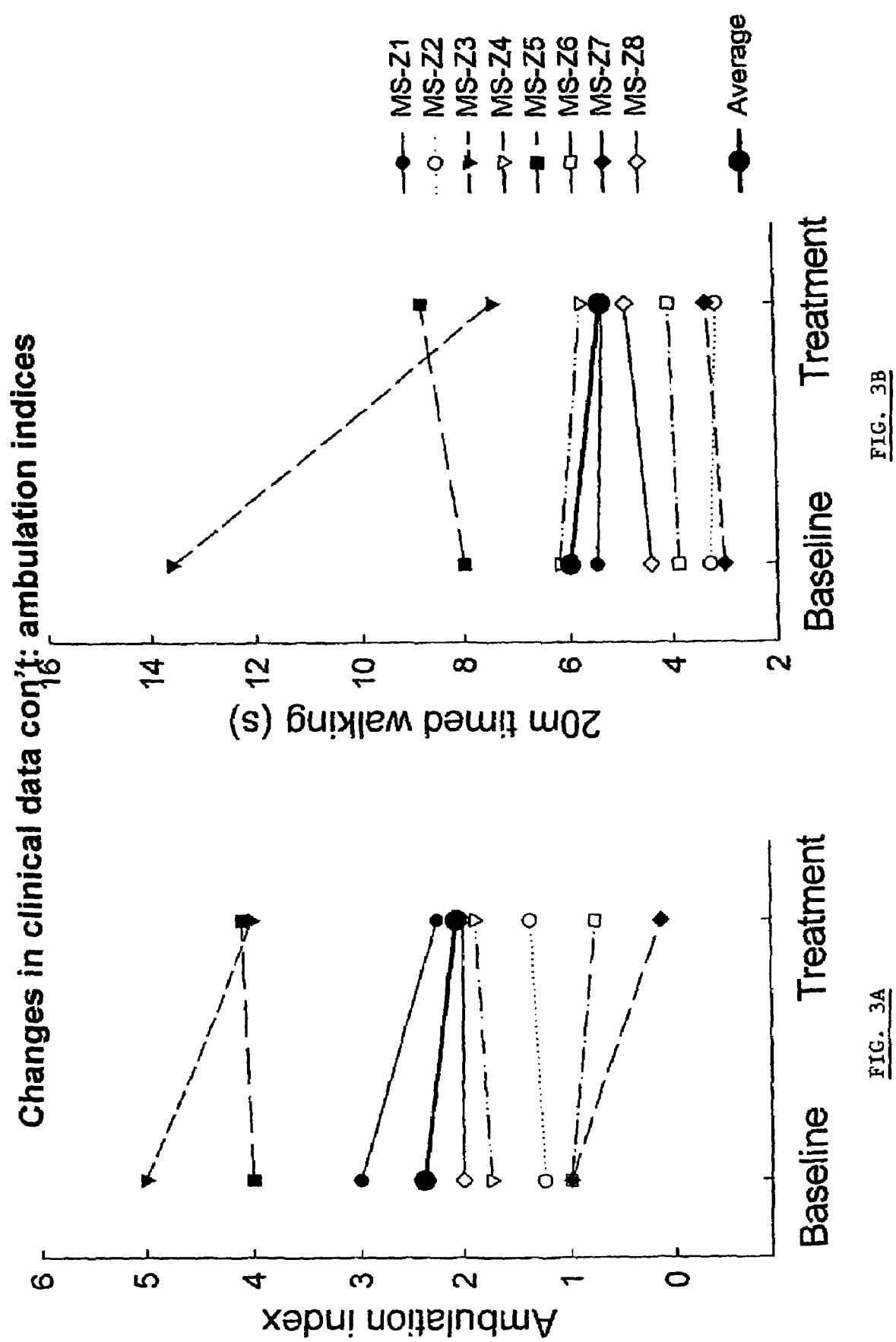
FIGS. 3A and 3B are graphs showing changes in neurological performance as measured by performance on the ambulation index (3A) and the timed 20 m walk (3B) between the baseline period and after combination therapy for the same subjects as in FIG. 1.
Figure 4A:
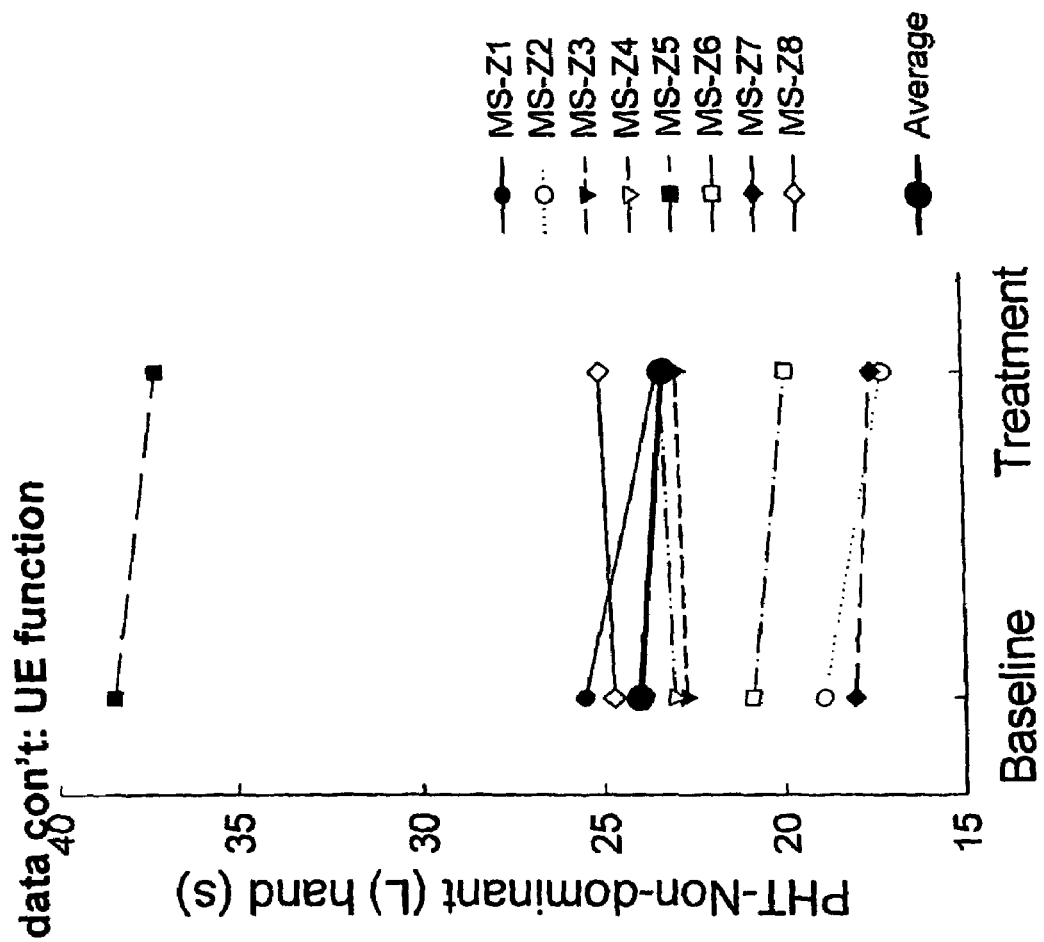
FIGS. 4A and 4B are graphs showing changes in neurological performance as measured by peg hole test times for dominant (4A) and non-dominant (4B) hands respectively, between the baseline period and after combination therapy for the same subjects as in FIG. 1.
Figure 4B:
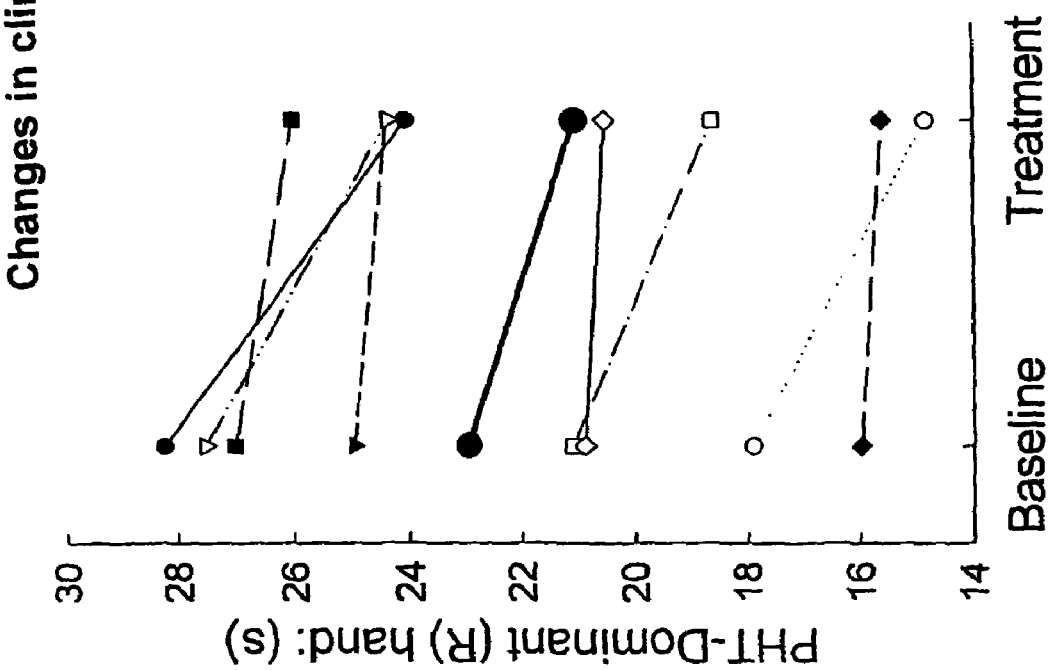

The combined administration of Interferon-beta and ZENAPAX® (daclizumab) led to almost complete cessation of disease activity and clinical improvement in seven of eight subjects. As can be seen in FIG. 1, seven of eight patients had either fewer or at least no increase in both new and total contrast enhancing lesions under the combination therapy as compared to the baseline period. Referring to FIG. 2A, four of eight subjects also demonstrated improvement on the EDSS under the combination therapy as compared to the baseline period. Referring to FIG. 2B, seven of eight subjects demonstrated improvement on the Scripps NRS. Referring to FIG. 3A, five of eight subjects demonstrated improved ambulation on the ambulation index. Referring to FIG. 3B, five of eight subjects either improved or had no change in a timed 20 m walk. Referring to FIG. 4A, all subjects demonstrated improved times with their dominant hand on the peg hole test. Referring to FIG. 4B, five of eight subjects also improved with their non-dominant hand on the peg hole test.

EXAMPLE 2

This example demonstrates the saturation of the Tac epitope following combination therapy and the parallel decrease in T-cell proliferation as compared to the baseline period.

Figure 5:
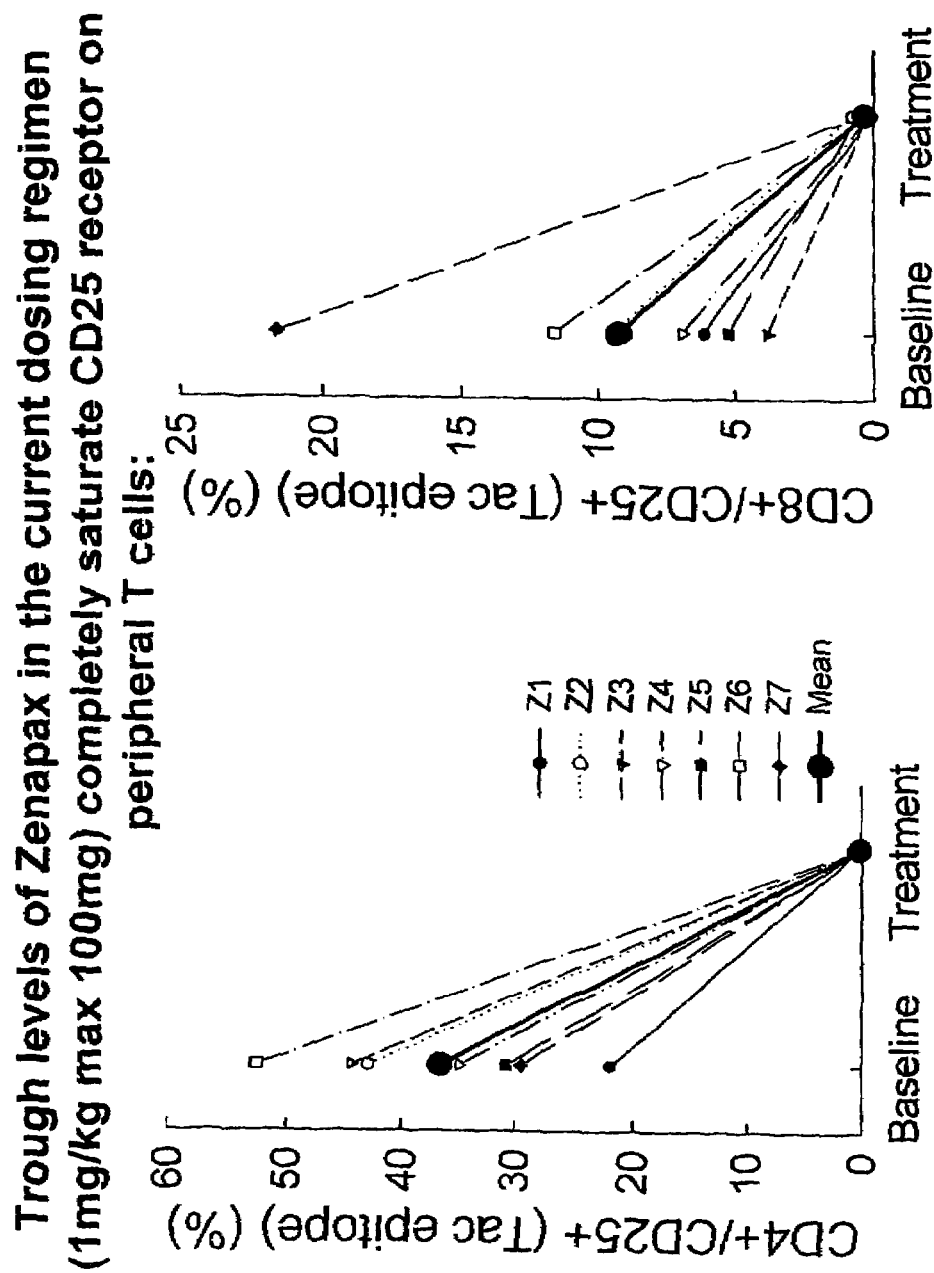
FIG. 5 is two graphs showing changes in the percentage of CD4/CD25 cells and CD8/CD25 cells expressing the Tac epitope between the baseline period and after combination therapy for seven of the subjects from FIG. 1.

Saturation of the Tac epitope was studied by flow cytometry. Referring to FIG. 5, the combined administration of interferon-beta with 1 mg/kg of ZENAPAX® (daclizumab) caused complete saturation of the Tac epitope on CD4/CD25 and CD8/CD25 T-cells.

Figures 6A, 6B:
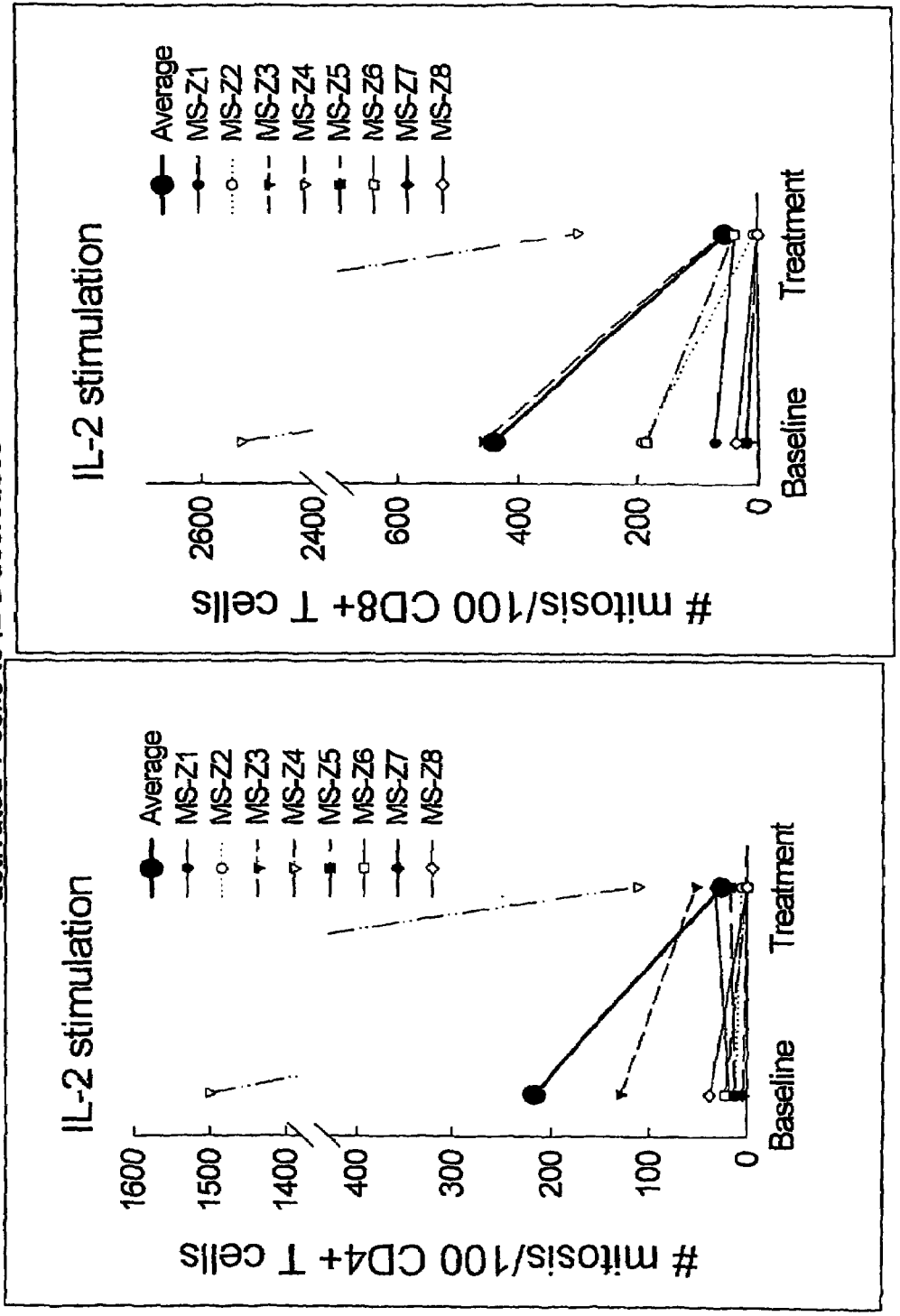
FIGS. 6A and 6B are graphs showing changes in the number of CD4 T-cell mitoses per one-hundred cells (6A) and CD8 T-cell mitoses per one-hundred cells (6B) between the baseline period and after combination therapy for the same subjects as in FIG. 1.

Proliferation of activated T-cells was measured by carboxyfluorescein succinimidyl ester (CFSE) fluorescence cell labeling and assessing the number of mitoses in CFSE-labeled cells by flow cytometry. Referring to FIG. 6A, six of eight subjects demonstrated decreased proliferation of CD4 T-cells. Referring to FIG. 6B, all subjects demonstrated a decrease in the proliferation of CD8 T-cells as compared to the baseline period.

EXAMPLE 3

This example demonstrates the unexpected upregulation of CTLA-4 caused by the combined administration of interferon-beta and an IL-2R antagonist.

CLTA-4 surface expression was measured by utilizing antibodies against CDLA-4 and flow cytometry. For each measurement of CTLA-4 surface expression, first, a 5 milliliter (ml) tube of whole blood in ethylene diamine tetra-acetic acid (EDTA) was obtained from each subject. Then, 42 ml of 1× lysing solution (4.2 ml 10 lysing solution+37.8 ml $H_2O$) was prepared from 10× stock prepared by dissolving in 1 liter of distilled water: 89.9 g $NH_4Cl$, 10.0 g KHCO3, 370.0 mg tetrasodium EDTA; and adjusting the solution to pH 7.3. 3 ml of blood was transferred by pipette into the 42 ml of 1× lysing solution (in 50 ml Falcon tubes). The mixture was allowed to stand at room temperature for 3-5 minutes. It was then centrifuged at 300× gravity for 5 minutes at room temperature. The supernatant was aspirated and the pellet was resuspended in 30 ml of cold X-vivo media. The resuspended mixture was centrifuged at 300× gravity for 5 minutes at 2-8° C., the supernatant was aspirated, and the pellet was resuspended in 2.5 ml of protein-enriched phosphate buffered saline (PBS) (10 ml of fetal calf serum (FCS) in 500 ml of 1×PBS). This cell suspension was divided into 200 µl aliquots in a 96 well plate, then centrifuged at 300× gravity for 5 minutes. The supernatant was discarded. Staining was performed by adding 10 microliter (µl)/well of prepared anti-CTLA-4 antibody mixture. The plate was then incubated for 30 minutes on ice in a dark container. Each well was washed with 200 µl of cold wash-buffer—mixed gently, and spun at 1000 rpm. Supernatants were removed and each well washed another 2 times with 200 µl of wash-buffer. After the last wash, the pellet was resuspended in 200 µl of staining buffer and analyzed by Fluorescence-Activated Cell Sorter (FACS)-Calibur. At least 10000 events gated on lymphocytes and 5000 events gated on monocytes were acquired.

Figure 7:
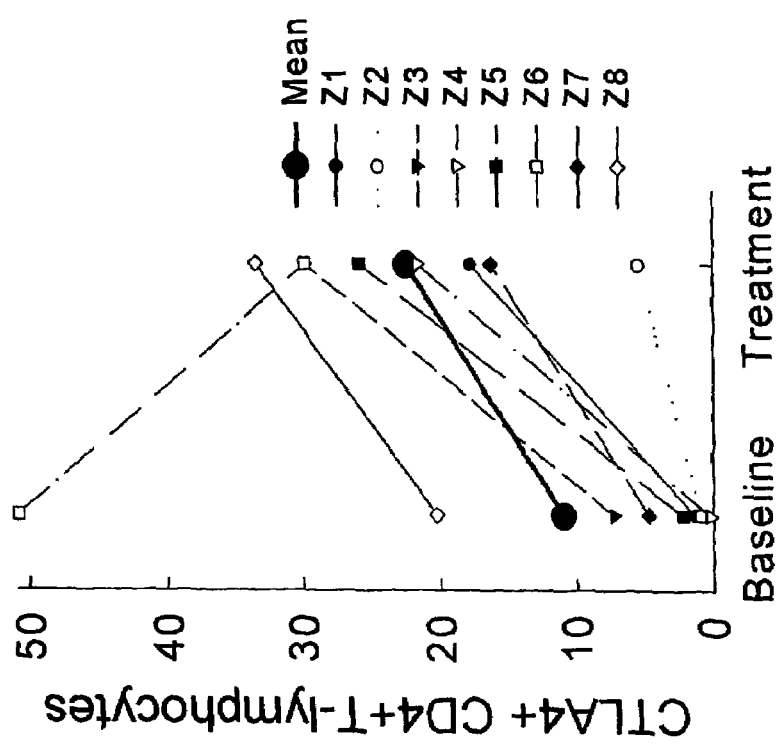
FIG. 7 is a graph showing changes in the number of CD4 T-cells expressing cytotoxic T lymphocyte-associated antigen 4 (CTLA-4) on their surface as measured by fluorescence-activated cell sorting of blood samples between the baseline period and after combination therapy for the same subjects as in FIG. 1.

Referring to FIG. 7, seven of eight subjects demonstrated significant upregulation of CTLA-4 during the combined therapy as compared to the baseline period.

EXAMPLE 4

This example illustrates treatment of subjects with MS with an IL-2R antagonist in the absence of concomitant treatment with interferon-beta.

Subjects meeting the inclusion and exclusion criteria of Example 1 are selected for treatment. For each subject, a baseline, 3-month period of treatment with interferon-beta is established. The interferon-beta is administered as indicated in the manufacturer's prescribing information. Four MRI scans are performed during this period on the schedule described in Example 1, as are the other diagnostic tests described in Example 1.

Combined interferon-beta/anti-Tac therapy begins after the baseline period is established and is performed for 5.5 months as described in Example 1. Diagnostic testing is also performed as described in Example 1.

Interferon-beta treatment is then discontinued, but monthly anti-Tac treatment is continued for an additional 22 months. During the first 10 months of anti-Tac monotherapy MRI scans and the other diagnostic tests are performed monthly. During months 11-22 of anti-Tac monotherapy at least 3 MRI scans are performed.

EXAMPLE 5

This example illustrates treatment of subjects diagnosed with MS with an IL-2R antagonist in the absence of concomitant treatment with interferon-beta and without necessarily having previously been treated with interferon-beta or having failed to respond to treatment with interferon-beta.

Subjects diagnosed with MS are selected for treatment. Subjects are administered the anti-Tac daclizumab every other week for one month, and then monthly.

The above-described examples merely provide examples of the disclosed method. They are not intended to be limiting in any way. Moreover, although embodiments of the disclosed method have been described herein in detail, it will be understood by those of skill in the art that variations may be made thereto without departing from the spirit of the invention or scope of the appended claims.

We claim:

1. A method of treating a subject that has multiple sclerosis comprising:
   administering to the subject that has multiple sclerosis a therapeutically effective amount of interferon-beta and a therapeutically effective amount of an antibody that specifically binds the interleukin 2 receptor,
   wherein the antibody that specifically binds the interleukin 2 receptor is administered every other week for two weeks and then monthly; once a week; every other week; or once a month,
   and wherein the subject has been treated previously with interferon-beta alone and has failed to respond to treatment with interferon-beta alone,
   thereby treating the subject.

2. The method of claim 1, wherein the interferon-beta comprises interferon-beta 1a.

3. The method of claim 1, wherein the interferon-beta comprises interferon-beta 1b.

4. The method of claim 1, wherein the interferon-beta comprises a combination of interferon-beta 1a and interferon-beta 1b.

5. The method of claim 1, wherein the antibody that specifically binds the interleukin 2 receptor is an anti-Tac antibody.

6. The method of claim 1, wherein the interferon-beta is administered weekly.

7. The method of claim 6, wherein the interferon-beta is interferon-beta 1b and the antibody that specifically binds the interleukin 2 receptor is anti-Tac.

8. The method of claim 1, wherein the interferon-beta is administered every other day.

9. The method of claim 1, wherein the antibody that specifically binds the interleukin 2 receptor is daclizumab.

10. The method of claim 1, wherein the multiple sclerosis is relapsing-remitting or secondary-progressive.

11. The method of claim 1, wherein the interferon-beta comprises interferon-beta 1a, interferon-beta 1b, or combinations thereof, and wherein the antibody that specifically binds the interleukin 2 receptor is anti-Tac.

12. The method of claim 9, wherein the daclizumab is administered at a dose of about 0.5 to about 8 mg/kg.

13. The method of claim 1, wherein the interferon-beta is administered subcutaneously.

14. A method of treating a subject that has multiple sclerosis, comprising:
    selecting a subject that has multiple sclerosis that has been previously treated with interferon-beta alone and has failed to respond to treatment with interferon-beta alone;
    administering to the subject that has multiple sclerosis daclizumab at a dose of 1 to 2 mg/kg every other week for two weeks and then monthly and administering to the subject interferon beta-1b at a dose of 0.006 mg to 2 mg by subcutaneous injection every other day.

15. A method of treating a subject with multiple sclerosis, comprising:
    selecting a subject that has multiple sclerosis that has been previously treated with interferon-beta alone and has failed to respond to treatment with interferon-beta alone; and
    administering to the subject with multiple sclerosis daclizumab at a dose of 1 to 2 mg/kg every other week for two weeks and then monthly and administering to the subject interferon beta-1a intramuscularly at a dose of 15 to 75 ug once a week.

16. The method of claim 1, wherein the antibody that specifically binds the interleukin 2 receptor is administered subcutaneously.

17. The method of claim 16, wherein the antibody that specifically binds the interleukin 2 receptor is administered every other week or every month.

18. The method of claim 1, wherein the antibody that specifically binds the interleukin 2 receptor is administered at a dose of about 0.5 to about 8 mg/kg.

19. The method of claim 16, wherein the antibody that specifically binds the interleukin 2 receptor is administered at a dose of about 0.5 to about 8 mg/kg.

20. The method of claim 1, wherein the antibody that specifically binds the interleukin 2 receptor is administered every other week for two weeks and then monthly.

21. The method of claim 12, wherein daclizumab is administered at a dose of about 2 mg/kg.

22. The method of claim 12, wherein daclizumab is administered at a dose of about 1 mg/kg.

* * * * *